US011896756B2

(12) United States Patent
Jardret et al.

(10) Patent No.: US 11,896,756 B2
(45) Date of Patent: Feb. 13, 2024

(54) NEGATIVE PRESSURE WOUND THERAPY INSTILLATION SYSTEM

(71) Applicant: DeRoyal Industries, Inc., Powell, TN (US)

(72) Inventors: Vincent Denis Jardret, Powell, TN (US); Jonathan Matthew Cayce, Knoxville, TN (US); Joe Lowell Smith, Powell, TN (US)

(73) Assignee: DeRoyal Industries, Inc., Powell, TN (US)

( * ) Notice: Subject to any disclaimer, the term of this patent is extended or adjusted under 35 U.S.C. 154(b) by 314 days.

(21) Appl. No.: 17/191,424

(22) Filed: Mar. 3, 2021

(65) Prior Publication Data

US 2021/0275730 A1   Sep. 9, 2021

Related U.S. Application Data

(60) Provisional application No. 62/984,499, filed on Mar. 3, 2020.

(51) Int. Cl.
*A61M 1/00* (2006.01)

(52) U.S. Cl.
CPC .............. *A61M 1/743* (2021.05); *A61M 1/73* (2021.05); *A61M 1/90* (2021.05); *A61M 2205/3344* (2013.01)

(58) Field of Classification Search
CPC .......... A61M 1/743; A61M 1/73; A61M 1/90; A61M 2205/3344; A61M 2205/3331; A61M 1/96; A61M 1/92
See application file for complete search history.

(56) References Cited

U.S. PATENT DOCUMENTS

| 7,195,624 | B2 | 3/2007 | Lockwood et al. |
| 7,532,953 | B2 | 5/2009 | Vogel |
| 7,608,066 | B2 | 10/2009 | Vogel |
| 7,837,673 | B2 | 11/2010 | Vogel |
| 7,883,494 | B2 | 2/2011 | Martin |
| 7,896,864 | B2 | 3/2011 | Lockwood et al. |
| 8,708,981 | B2 | 4/2014 | Locke et al. |
| 9,757,500 | B2 | 9/2017 | Locke et al. |
| 9,789,234 | B2 | 10/2017 | Pratt et al. |
| 9,907,939 | B2 | 3/2018 | Randolph et al. |

(Continued)

FOREIGN PATENT DOCUMENTS

EP     0182248 A2 *  5/1986  .......... A61M 16/008

OTHER PUBLICATIONS

International Search Report and Written Opinion for PCT/US21/20714, dated May 20, 2021, 14 pages.

*Primary Examiner* — Susan S Su
*Assistant Examiner* — Eric Rassavong
(74) *Attorney, Agent, or Firm* — Luedeka Neely, P.C.

(57) ABSTRACT

A system for delivering reduced pressure and irrigation fluid to a wound site. The system includes a primary pressure source for delivering reduced pressure through a first lumen, a secondary pressure source for delivering secondary pressure through a second lumen, and an irrigation fluid source. A valve system is operable to selectively couple the secondary pressure source to the second lumen for delivering the secondary pressure to a wound site and selectively couple the fluid source to the second lumen for delivering the irrigation fluid to the wound site.

21 Claims, 3 Drawing Sheets

(56) References Cited

U.S. PATENT DOCUMENTS

| | | | |
|---|---|---|---|
| 9,907,940 B2 | 3/2018 | Pratt et al. | |
| 10,086,119 B2 | 10/2018 | Pratt et al. | |
| 10,124,095 B2 * | 11/2018 | Locke | A61M 1/74 |
| 10,350,336 B2 | 7/2019 | Luckemeyer et al. | |
| 10,350,338 B2 | 7/2019 | Tout et al. | |
| 10,391,208 B2 | 8/2019 | Robinson et al. | |
| 2002/0198503 A1 * | 12/2002 | Risk, Jr. | A61M 1/74 |
| | | | 604/315 |
| 2008/0269651 A1 | 10/2008 | Warlick et al. | |
| 2009/0012483 A1 | 1/2009 | Blott et al. | |
| 2012/0271257 A1 * | 10/2012 | Coulthard | A61M 1/74 |
| | | | 604/319 |
| 2012/0302976 A1 | 11/2012 | Locke et al. | |
| 2012/0302979 A1 * | 11/2012 | Locke | A61M 1/915 |
| | | | 604/319 |
| 2013/0131616 A1 * | 5/2013 | Locke | A61M 1/918 |
| | | | 604/319 |
| 2013/0204210 A1 * | 8/2013 | Pratt | A61M 1/85 |
| | | | 604/290 |
| 2016/0199550 A1 * | 7/2016 | Seddon | A61F 13/00068 |
| | | | 604/319 |
| 2016/0354535 A1 * | 12/2016 | Blott | A61N 5/025 |
| 2018/0140822 A1 | 5/2018 | Robinson et al. | |
| 2018/0185629 A1 | 7/2018 | Luckemeyer et al. | |
| 2018/0190155 A1 * | 7/2018 | Segall | G09B 23/303 |
| 2019/0201595 A1 | 7/2019 | Jardret et al. | |
| 2020/0038249 A1 * | 2/2020 | Pratt | A61M 1/95 |

\* cited by examiner

NEGATIVE PRESSURE WOUND THERAPY INSTILLATION SYSTEM

CROSS REFERENCE TO RELATED APPLICATION

This application claims priority to U.S. Provisional Application Ser. No. 62/984,499 filed Mar. 3, 2020, entitled "Negative Pressure Wound Therapy Instillation System," the entire contents of which is incorporated herein by reference.

FIELD

This disclosure relates to the field of negative pressure wound therapy. More particularly, this disclosure relates to a system for managing delivering both reduced pressure and an irrigation fluid to a sealed wound enclosure.

BACKGROUND

The purpose of negative pressure wound therapy (NPWT) is to apply a reduced pressure (also referred to as negative or vacuum pressure) to a wound to stimulate healing and remove excess exudate from the wound bed. During certain NPWT treatments, it has been found that flooding the wound bed with specific solutions provides benefits to the healing process of certain wounds. This process is often referred to as "instillation" or "irrigation" therapy. It should be understood that "instillation" and "irrigation" may be used interchangeably herein.

While instillation therapy is believed to provide additional benefits compared to traditional NPWT, current commercially available systems present several drawbacks. In particular, some systems "flood" the wound while completely releasing pressure. This results in the foam/wound filler of the dressing expanding and pushing on the adherent film used to seal the dressing to the patient. This force can result in damage to the dressing seal, which compromises the ability to re-establish NPWT and forces the caregiver to change the dressing more frequently. The loosening of the seal to the dressing can also cause the dressing to leak, which results in caregivers having to clean fluids on and around the patient. Further, damage to the dressing seal results in the peri skin of the patient becoming wet. Moisture to the peri skin can cause maceration of the peri skin and can lead to peri-skin breakdown, which enlarges the treated wound.

Many currently available commercial systems also require electronic communication between the source of negative pressure and the instillation fluid source. Thus, special processing and communication equipment is needed to perform instillation treatment in combination with standard NPWT. This raises the cost of currently available systems and increases the risk for malfunctions.

Yet another drawback is that instillation systems are typically not compatible with dual lumen NPWT systems that include a vacuum lumen (exudate removal) and a pressure sensing or air lumen. In this regard, while the primary function of NPWT is to apply the negative pressure to the wound bed, it is also to facilitate the removal of exudate from the wound bed. However, since the purpose of instillation is to allow fluids to dwell within the wound bed enclosure, the negative pressure to the wound bed and resulting removal of exudate from the wound bed to a collection canister has traditionally been required to be turned off for instillation to be effective. As noted above, interruption of NPWT resulting in a complete release of the pressure at the wound bed can create several issues for both the clinical staff and the patient.

What is needed is an affordable NPWT system that enables instillation to be applied easily to a wound dressing while limiting damages incurred to the dressing during the instillation and while maintaining the wound under negative pressure.

SUMMARY

The above and other needs are met by a wound therapy system for delivering reduced pressure and irrigation fluid to a wound site. The system includes a wound enclosure configured to form a substantially sealed volume around the wound, a wound exudate collection canister; and a primary pressure source configured to deliver the reduced pressure to the substantially sealed volume and deliver exudate collected from the wound site to the wound exudate collection canister through a first lumen. The system further includes a secondary pressure source configured to deliver a secondary pressure to the substantially sealed volume through a second lumen and a fluid source configured to deliver irrigation fluid to the substantially sealed volume through the second lumen. A valve system is fluidly coupled to the secondary pressure source and the fluid source that is operable to selectively couple the secondary pressure source to the second lumen for delivering the secondary pressure to the substantially sealed volume and selectively couple the fluid source to the second lumen for delivering the irrigation fluid to the substantially sealed volume. The therapy system further includes a first mode of operation in which the primary pressure source delivers reduced pressure to the substantially sealed volume through the first lumen while the secondary pressure source delivers the secondary pressure to the substantially sealed volume through the second lumen and a second mode of operation in which the primary pressure source delivers reduced pressure to the substantially sealed volume through the first lumen while the fluid source delivers irrigation fluid to the substantially sealed volume through the second lumen.

According to certain embodiments, the wound therapy system further includes a flushing mode of operation in which the primary pressure source delivers reduced pressure to the substantially sealed volume through the first lumen while simultaneously delivering secondary pressure from the secondary pressure source and irrigation fluid from the fluid source to the substantially sealed volume through the second lumen.

According to certain embodiments, the valve system is further operable to fluidly couple the secondary pressure source to the first lumen such that the secondary pressure delivered from the secondary pressure source bypasses the wound enclosure during the second mode of operation.

According to certain embodiments, the wound therapy system further includes a dwelling mode of operation in which the primary pressure source delivers reduced pressure to the substantially sealed volume through the first lumen while the valve system prevents the secondary pressure source from delivering the secondary pressure to the substantially sealed volume and prevents the fluid source from delivering irrigation fluid to the substantially sealed volume. In some embodiments, the valve system is configured to fluidly couple the secondary pressure source to the first lumen such that the secondary pressure delivered from the secondary pressure source bypasses the wound enclosure during the dwelling mode of operation. In some embodiments, the system further includes a pressure sensor for measuring pressure within at least one of the first lumen and the second lumen and a controller configured to receive pressure measurements from the pressure sensor and to communicate with the valve system for switching between the first, second, and dwelling modes of operation based at least in part on the pressure measurements received from the pressure sensor. In some embodiments, the primary pressure source is configured to deliver variable reduced pressure to the substantially sealed volume according to a variable pressure cycle during at least the dwelling mode of operation.

According to certain embodiments, the valve system is operable to switch from the first mode of operation to the second mode of operation based at least in part on predetermined time intervals.

According to certain embodiments, a length of time in which the valve system is in the second mode of operation is based at least in part on a size measurement of the wound site.

According to certain embodiments, the wound therapy system further includes an irrigation fluid collection canister fluidly connected to the first lumen between the wound exudate collection canister and the wound enclosure for collecting irrigation fluid from the wound site.

According to certain embodiments, the wound therapy system further includes a fluid sensor configured and positioned for detecting irrigation fluid in the first lumen.

According to another aspect of the disclosure, a method for delivering reduced pressure and irrigation fluid to a wound site includes providing a wound therapy system having a primary pressure source, a secondary pressure source, and a fluid source; delivering secondary pressure from the secondary pressure source to the wound enclosure through a second lumen during a first mode of operation; delivering irrigation fluid from the fluid source to the wound enclosure through the second lumen during a second mode of operation; preventing the delivery of both the secondary pressure and the irrigation fluid to the wound enclosure during a third mode of operation; and continuously delivering reduced pressure from the primary pressure source to the wound enclosure through a first lumen during each of the first mode of operation, the second mode of operation, and the third mode of operation.

According to certain embodiments, the secondary pressure from the secondary pressure source is delivered to the first lumen while bypassing the wound enclosure during the second mode of operation and the third mode of operation. In some embodiments, the method further includes selectively delivering secondary pressure to the first lumen for managing a pressure in the first lumen during the third mode of operation.

According to certain embodiments, the method further includes switching from the first mode of operation to the second mode of operation to initiate an irrigation therapy session; switching from the second mode of operation to the third mode of operation to perform the irrigation therapy session; and switching from the third mode of operation back to the first mode of operation to end the irrigation therapy session. In some embodiments, the switching from the second mode of operation to the third mode of operation is based at least in part on detecting irrigation fluid in the second lumen.

According to certain embodiments, the method further includes delivering secondary pressure and irrigation fluid to the wound enclosure through the second lumen during a fourth mode of operation.

According to yet another aspect of the disclosure, an irrigation valve system for a wound therapy system is provided. The valve system includes a first valve for fluidly coupling a fluid source to a second lumen with the first valve including an open position for delivering irrigation fluid from the fluid source to the wound enclosure through the second lumen and a closed position for preventing irrigation fluid from being delivered to the wound enclosure through the second lumen. The valve system further includes a second valve for fluidly coupling a secondary pressure source to the second lumen with the second valve including an open position for delivering secondary pressure from the secondary pressure source to the wound enclosure through the second lumen and a closed position for preventing secondary pressure from being delivered to the wound enclosure through the second lumen. The valve system enables continuous operation of the primary pressure source for delivering reduced pressure to the wound enclosure through the first lumen while the valve system is selectively delivering one of the irrigation fluid and the secondary pressure to the wound enclosure through the second lumen.

According to certain embodiments, the irrigation valve system further includes a third valve for fluidly coupling the secondary pressure source to the first lumen for delivering secondary pressure from the secondary pressure source to the first lumen while bypassing the wound enclosure when the third valve is in an open position and the second valve is in a closed position.

According to certain embodiments, the irrigation valve system includes a communicator for communicating to the primary pressure source when it has initiated an irrigation therapy session by coupling the fluid source to the second lumen.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
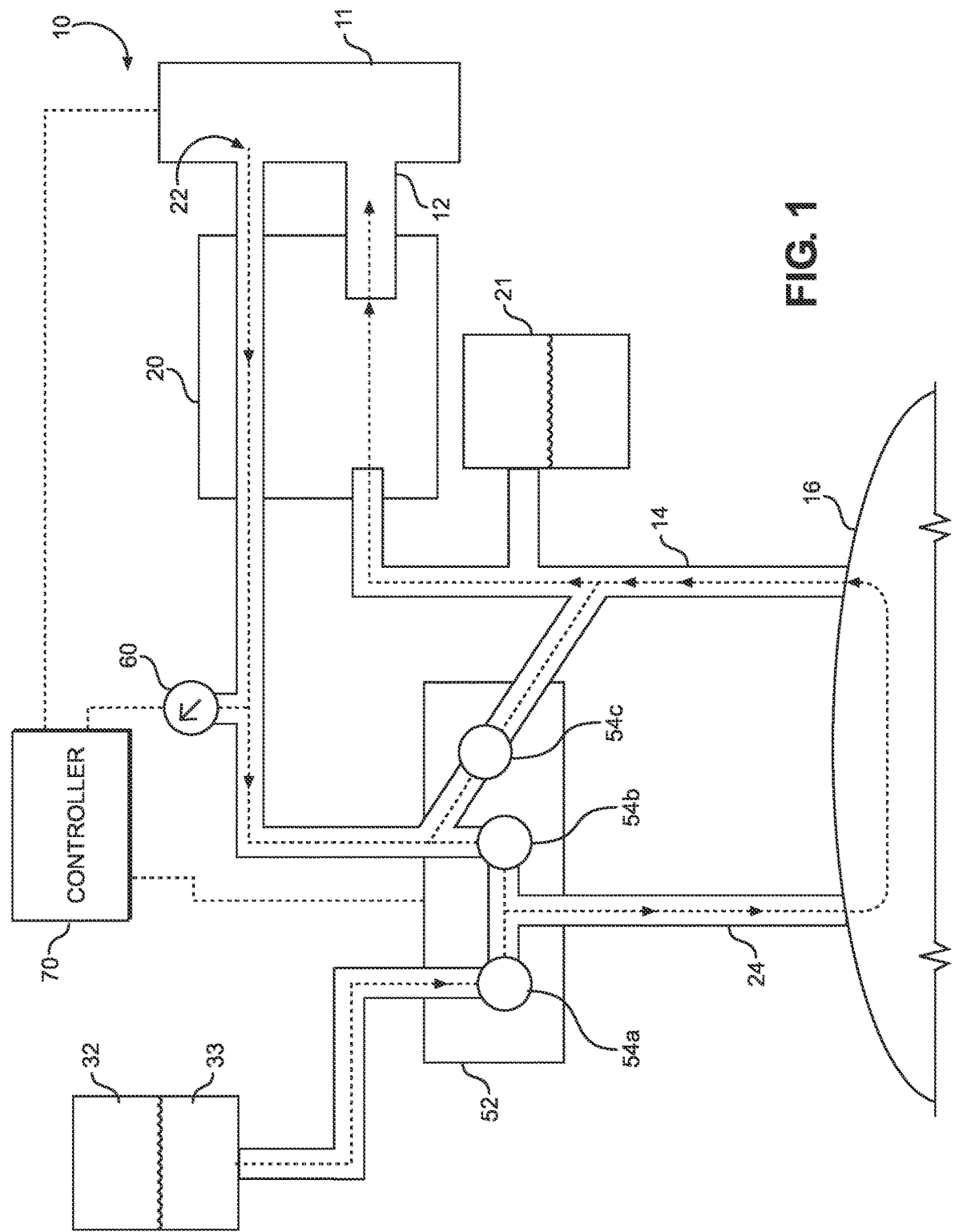
FIG. 1 depicts a functional block diagram of an NPWT system according to one embodiment of the disclosure.

Referring to FIG. 1, the present disclosure is directed to a NPWT system 10 having a reduced pressure source 12, a secondary pressure source 22, and a fluid source 32. As understood in the art, the reduced pressure source 12 is configured to deliver reduced pressure along a first fluid flow path to a wound enclosure 16 that is to be disposed at a wound site while the secondary pressure source 22 is configured to deliver secondary pressure to the wound enclosure 16 along a second fluid flow path. In certain embodiments, and as depicted in FIG. 1, a single vacuum pump 11 may provide both the reduced pressure source 12 and secondary pressure source 22. According to this embodiment, and as described in detail in U.S. patent application Ser. No. 16/235,113, which is commonly assigned to the assignee of the present application and the disclosure of which is incorporated by reference herein in its entirety, the inlet of the vacuum pump serves as the reduced pressure source 12 while the outlet of the vacuum pump serves as the secondary pressure source 22. In other embodiments, the secondary pressure source 22 could be a separate component such as a second pump. The secondary pressure source can also be the outside/atmospheric air such as introduced into the system 10 from a valve disposed along the second fluid flow path.

As also understood in the art, the wound enclosure 16 typically includes a foam/gauze material for filling the open wound and a thin film (typically a polyurethane film) adhesively applied to a patient's skin for forming a substantially sealed volume around the wound site. A first lumen 14 is fluidly coupled to the wound enclosure 16 for delivering the reduced pressure from the reduced pressure source 12 to the wound enclosure 16. A waste canister 20 is fluidly coupled with the reduced pressure source 12 and the first lumen for receiving exudate collected from the wound site as a result of the reduced pressure being delivered to the wound enclosure 16 from the reduced pressure source 12 along the first fluid flow path. A second lumen 24 is also fluidly coupled to the wound enclosure 16 for delivering one of secondary pressure (e.g., positive pressure or otherwise a pressure between the reduced pressure of the reduced pressure source and atmospheric pressure) and irrigation fluid to the wound enclosure 16 along the second fluid flow path as described further below. In certain embodiments, the first lumen 14 and second lumen 24 could be included at least in part in dual lumen tubing as known in the art. In other embodiments, the first lumen 14 and second lumen 24 could be provided in separate tubing.

For purposes of the present disclosure, it is noted that "fluidly coupled" broadly refers to two or more structures or fluid passages being in fluid communication with each other while recognizing the potential for intervening components being used to fluidly connect the particular structures or fluid passages. For example, the waste canister 20 as described above may be referred to as "fluidly coupled" to the wound enclosure 16 despite intervening tubing being used to connect the components together along the first fluid flow path. Similarly, the first lumen 14 may be referred to as being used for "fluidly coupling" the wound enclosure 16 to the reduced pressure source 12 despite the canister 20 being disposed along the fluid flow path between the first lumen and the reduced pressure source 12. On the other hand, "fluidly connected" (or "fluidly connecting") may be used to refer to a more direct fluid communication between two components. For example, the first lumen may be referred to as being fluidly connected to the wound enclosure 16 because one end of the tubing containing the first lumen 14 is in direct fluid communication with the wound enclosure 16.

With continued reference to FIG. 1, the NPWT system 10 includes a valve system 52 fluidly coupled to the secondary pressure source 22, the fluid source 32, and the second lumen 24. The valve system 52 is configured to selectively deliver one of secondary pressure from the secondary pressure source 22 to the wound enclosure 16 and an irrigation fluid 33 from the fluid source 32 to the wound enclosure 16. In this regard, the valve system 52 is configured to (1) fluidly couple the secondary pressure source 22 to the second lumen 24 when it is desired to deliver secondary pressure to the wound enclosure 16; and (2) fluidly couple the fluid source 32 to the second lumen 24 when it is desired to deliver the irrigation fluid 33 to the wound enclosure 16.

Utilizing valve system 52, the NPWT preferably provides for at least four modes of operation for the NPWT system 10: (1) a first mode of operation (which may also be referred to herein as a "standard" NPWT mode of operation) in which the reduced pressure source 12 delivers reduced pressure to the wound enclosure 16 through reduced pressure tubing 14 while the valve system 52 fluidly couples the secondary pressure source 22 to the second lumen 24 for delivering secondary pressure (i.e., positive pressure) to the wound enclosure 16; (2) a second mode of operation (which may also be referred to herein as a "flooding" mode of operation) in which the reduced pressure source 12 delivers primary pressure to the wound enclosure through first lumen 14 while the valve system 52 fluidly couples the fluid source 32 to the second lumen 24 for delivering irrigation fluid 33 to the would enclosure 16; (3) a third mode of operation (which may also be referred to herein as a "dwelling" mode of operation) in which the reduced pressure source 12 delivers primary pressure to the wound enclosure 16 through first lumen 14 while the valve system 52 disconnects/decouples both the secondary source 22 and the fluid source 32 from the second lumen 24 (i.e., the valve system 52 prevents both the secondary pressure and the irrigation fluid from being delivered to the wound enclosure 16); and (4) a fourth mode of operation (which may also be referred to herein as a "flushing" mode of operation) in which the reduced pressure source 12 delivers primary pressure to the wound enclosure 16 through reduced pressure tubing 14 while the valve system fluidly couples both the secondary pressure source 22 and the fluid source 32 to the second lumen 24 for delivering both secondary pressure and the irrigation fluid 33 to the wound enclosure 16.

In each of the modes of operation described above, the reduced pressure source is able to continuously deliver reduced pressure to the wound enclosure through the first lumen 14. According to certain embodiments, the continuous delivery of reduced pressure is assisted by the valve system 52 also preferably being configured to fluidly couple the secondary pressure source 22 to the fluid flow path of the reduced pressure source 12 (i.e., first lumen 14) when the secondary pressure source 22 is disconnected from the second lumen 24. In other words, in both the second and third modes of operation described above, the valve system 52 is preferably configured to be able to route the secondary pressure from the secondary pressure source 22 to the reduced pressure fluid flow path such that the secondary pressure bypasses the wound enclosure 16 without having to be vented to the atmosphere.

One exemplary embodiment of valve system 52 is depicted in FIG. 1 as including valves 54a, 54b, and 54c. As shown, valve 54a fluidly couples the fluid source 32 to second lumen 24, valve 54b fluidly couples secondary pressure source 22 to second lumen 24, and valve 54c fluidly couples secondary pressure source 22 to first lumen 14. For the first mode of operation, valve 54a is in a closed position to prevent irrigation fluid from flowing to the second lumen 24, valve 54b is in an open position to fluidly couple the secondary pressure source 22 to the second lumen 24 for delivering secondary pressure to the wound enclosure 16, and valve 54c is in a closed position for preventing the secondary pressure from the secondary pressure source 22 from bypassing the wound enclosure 16 through first lumen 14. According to some embodiments, and because the first mode of operation is generally considered the standard NPWT treatment, valve 54a may be configured to be normally closed, valve 54b may be configured to be normally open, and valve 54c may be configured to be normally closed.

For the second mode of operation, valve 54a is moved to an open position for fluidly coupling the fluid source 32 to the second lumen 24, valve 54b is in a closed position for disconnecting the secondary pressure source 22 from the second lumen 24, and valve 54c is in an open position for fluidly coupling the secondary pressure source 22 to the first lumen 14. The second mode of operation thus delivers irrigation fluid 33 to the wound enclosure 16 while reduced pressure is also being delivered to the wound enclosure 16.

In the third mode of operation, valve 54a is in a closed position to prevent irrigation fluid from flowing to the second lumen 24, valve 54b is in a closed position for preventing the secondary pressure from flowing to the second lumen 24, and valve 54c is in an open position for fluidly coupling the secondary pressure source 22 to the first lumen. Thus, in the second mode of operation, only reduced pressure from the reduced pressure source 12 is being delivered to the wound enclosure 16. The third mode of operation is intended to allow the irrigation fluid 33 delivered during the second mode of operation to dwell in the wound enclosure 16.

In the fourth mode of operation, valve 54a is in an open position for fluidly coupling the fluid source 32 to the second lumen 24, valve 54b is also in an open position for fluidly coupling the secondary pressure source 22 to the second lumen 24, and valve 54c is in a closed position for preventing the secondary pressure from the secondary pressure source 22 from bypassing the wound enclosure 16 through first lumen 14. Thus, in the fourth mode of operation, irrigation fluid 33 and secondary pressure are delivered simultaneously to the wound enclosure 16. In effect, the fourth mode of operation operates to "flush" the wound enclosure 16 with irrigation fluid 33 with the extraction of the fluid 33 being assisted/controlled by the secondary pressure source 22.

It should be understood that valve system 52 as depicted in FIG. 1 having three valves 54a, 54b, and 54c is an exemplary valve system and other combinations of valves can be implemented within the scope of the present disclosure. In particular, two or more valves 54a, 54b, and 54c could be combined into a single valve. For example, valve 54b and valve 54c of FIG. 1 could be combined into a single diverter valve or two-way ball valve for fluidly coupling the secondary pressure source 22 to either the second lumen 24 or the first lumen 14.

According to another aspect of the disclosure, and with continued reference to FIG. 1, an additional waste canister 21 may be provided between canister 20 and the wound enclosure 16 along the first lumen 14 path to collect irrigation fluid removed from the wound enclosure 16.

According to certain embodiments, the valve system 52 is operable to switch the system 10 between the different modes of operation based on settings established by the user (e.g., caregiver). For example, valve system 52 may be programmed to switch between a standard NPWT therapy session and an irrigation therapy session based on predetermined time intervals established by the user. When an irrigation therapy session is initiated, the valve system 52 would (1) switch from the first mode of operation (standard NPWT) to the second mode of operation (flooding of the wound with irrigation fluid); (2) switch from the second mode of operation to the third mode of operation to provide for dwelling of the fluid in the wound enclosure 16 for a time specified by the system settings; and (3) switch back to the first mode of operation, which will flush irrigation fluid 33 from the wound to the waste canister 20 and/or 21, to end the irrigation therapy session.

The amount of time in which the valve system 52 is in the second mode of operation may also be based on a predetermined time interval. The predetermined time interval for the second mode of operation may be based at least in part on the size of the wound being treated. In this regard, larger wounds may require longer periods of time in the second mode of operation to sufficiently soak the wound dressing with irrigation fluid. Alternately, the amount of time in which the valve system 52 is in the second mode of operation may be based on the detection of irrigation fluid in the first lumen 14, which would indicate that the wound enclosure 16 is substantially filled with irrigation fluid 33. Various manners in which fluid 33 may be detected in the first lumen 14 are described below.

In other embodiments, valve system 52 is operable to switch the system 10 between the different modes of operation based on pressure measurements (such as pressure measurements received from pressure sensor 60 shown in FIG. 1 and described further below) during a variable pressure therapy established by the vacuum pump 11. For example, when it is determined that the pressure within the system during the first mode of operation is below a certain threshold (i.e., the low-pressure portion of the variable cycle), the valve system 52 is triggered to initiate an irrigation therapy session as described above. The valve system may similarly be triggered to end the irrigation therapy session when the pressure of the primary pressure source 12 increases (i.e., goes back to the high-pressure portion of the variable cycle).

According to another aspect of the disclosure, and with continued reference to FIG. 1, a pressure sensor 60 is disposed along the second fluid flow path preferably between the valve system 52 and the secondary pressure source 22. The pressure sensor 60, valve system 52, and pump 11 are in communication with a controller 70. During the first mode of operation, pressure sensor 60 is configured to measure the pressure at the wound enclosure 16 while no irrigation fluid is present inside the second lumen 24 (i.e., during standard dual lumen NPWT therapy). During the second mode of operation (i.e., irrigation fluid being delivered to the wound enclosure and the secondary pressure being routed to the first lumen) and the third mode of operation with valve 54c open, pressure sensor 60 is able to measure the pressure in the first lumen 14 along the connection point with the valve system 52. Based on the pressure measurements received by controller 70 from pressure sensor 60 during the second and third mode of operation, the system 10 may facilitate the flow of any irrigation fluid 33 in the first lumen 14 toward the canister 20 and/or canister 21 by activating the secondary pressure source 22 and allowing the secondary pressure to flow through valve 54c to the first lumen 14. Thus, during the third mode of operation, the wound dressing of wound enclosure 16 is able to dwell in the irrigation fluid 33 while the primary pressure source 12 and secondary pressure source 22 ensures the desired pressure is applied up to the connection point between the first lumen 14 and the valve system 52.

According to some embodiments, the NPWT system 10 may facilitate the distribution of the irrigation fluid 33 within the wound enclosure 16 by applying different pressures to the wound enclosure 16 in a cyclic fashion, for example, the pressure may be cycled from −125 mmHg for two minutes and −20 mmHg for two minutes several times while irrigation fluid 33 is dwelling in the wound enclosure 16 during the third mode of operation.

Figure 2:
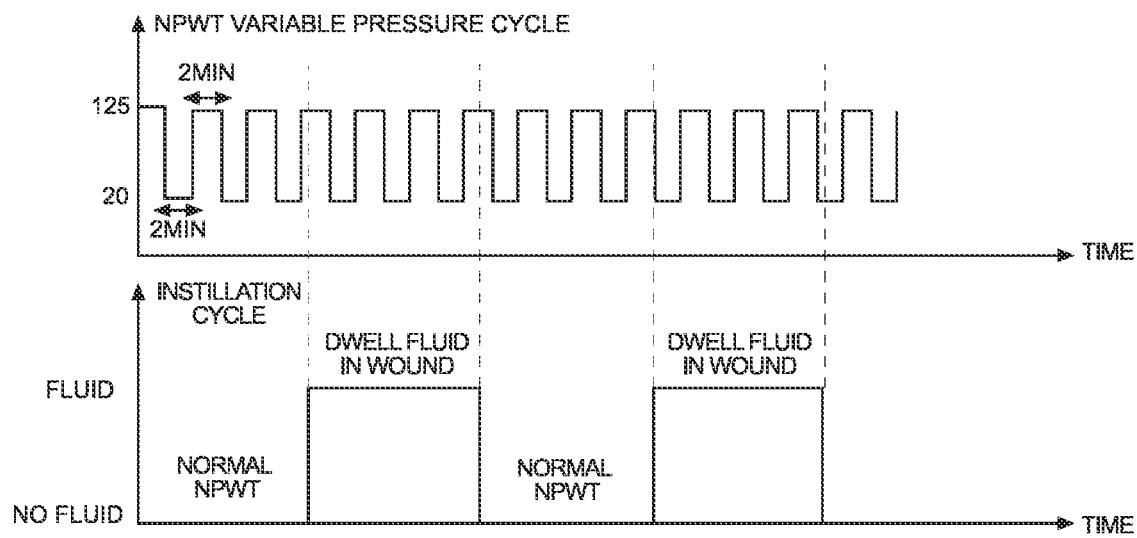
FIG. 2 depicts a graphical representation of a variable pressure treatment cycle and installation treatment cycle according to one embodiment of the disclosure.

According to some embodiments, the NPWT system 10 can be set to apply a variable or intermittent pressure to the wound enclosure 16 through primary lumen 14 during the irrigation therapy treatment session. During the variable therapy, the valve system 52 can be configured to apply a cycle between the first mode of operation and the third mode of operation. For example, and with reference to FIG. 2, the primary pressure source 12 is configured to cycle between −125 mmHG and −20 mmHG every two minutes to deliver the variable pressure therapy through first lumen 14. The valve system 52 is then configured to cycle between the first mode of operation and the third mode of operation while the primary pressure source 12 continues to deliver the variable reduced pressure therapy. In certain embodiments, the valve system 52 is configured to be in the third mode of operation for a longer cycle (e.g., allowing irrigation fluid 33 to dwell in the wound enclosure 16 for about 10-12 minutes) than the time period in which the primary pressure source 12 cycles between different pressures (e.g., every two minutes). The application of several NPWT pressure cycles while the wound is flooded with irrigation fluid 33 facilitates the flow of the irrigation fluid 33 within the wound enclosure 16 and associated dressing (similar to how squeezing and releasing a sponge has the effect of distributing the soap over the entire sponge). In other words, the pressure cycle acts as a squeezing mechanism inside the wound enclosure 16 and enables the irrigation fluid 33 to spread over the entire volume of the wound dressing within the wound enclosure 16.

Figure 3:
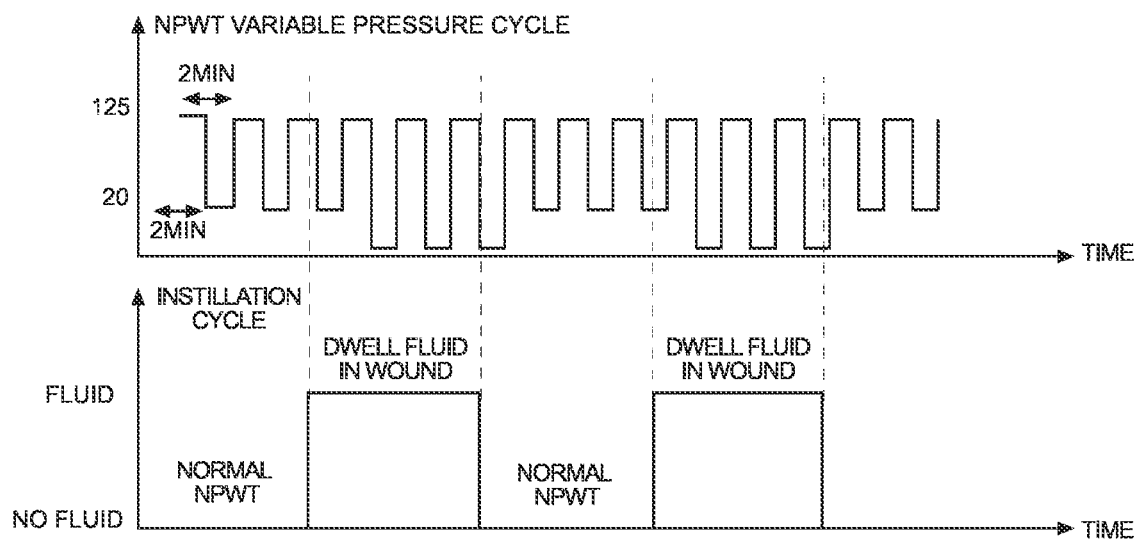
FIG. 3 depicts a graphical representation of a variable pressure treatment cycle and installation treatment cycle according to another embodiment of the disclosure.

According to certain embodiments, valve system 52 is configured to communicate to the vacuum pump 11/reduced pressure source 12 the current mode of operation of system 10 such that the vacuum pump 11 is operable to modify the therapy settings based on the communications received from the valve system 52. For example, the valve system 20 may send a start signal to the vacuum pump 11 indicating the second mode of operation (i.e., delivering installation fluid to the wound enclosure) has begun. The start signal then triggers the vacuum pump 11 to apply a variable reduced pressure cycle with the maximum pressure set by the user at the pump 11 and the low pressure would be communicated to the vacuum pump 11 by the valve system 52. With reference to FIG. 4 as compared to FIG. 3, the low pressure during the instillation cycle may be at or around −20 mmHg (FIG. 3), or a preferred pressure slightly below 0 (FIG. 4), adequate for instillation. Valve system 52 may also send a signal to the vacuum pump 11 when installation has been completed (i.e., a return to the first mode of operation) to resume the normal therapy settings selected by the user.

According to some embodiments, while the valve system 52 is flooding the wound with irrigation fluid 33 in the second mode of operation, the system 10 detects when the fluid has filled the wound enclosure 16 and part of the first lumen 14. In this regard, the presence of irrigation fluid 33 in the first lumen 14 indicates that the wound enclosure 16 should be generally filled with irrigation fluid 33. Upon detection of irrigation fluid in the first lumen 14, a signal is sent to the valve system 52 to switch from the second mode of operation to the third mode of operation to allow the irrigation fluid 33 to dwell in the wound enclosure 16.

According to some embodiments, the NPWT system 10 detects the presence of fluid in the wound enclosure 16 and first lumen 14 by comparing different pressure readings within the system. For example, in certain embodiments, the presence/amount of irrigation fluid 33 within the wound enclosure 16 and first lumen 14 may be determined by monitoring the difference between the wound pressure using sensor 60 and the vacuum/canister pressure established by the pump settings. In other embodiments, a pressure sensor could also be positioned in the irrigation fluid 33 flow path between the fluid source 32 and valve system 52 (i.e., fluid source flow line from fluid source 32 to valve system 52) for determining the amount of irrigation fluid 33 in the wound enclosure 16 and first lumen 14 by comparing the wound pressure with the pressure of pressure of fluid source flow line.

Alternatively, a fluid sensor could be connected to the first lumen 14 between the wound enclosure 16 and canister 20, 21 for detecting the presence of fluid. For example, the sensor could include two electrodes in contact with the internal volume of the first lumen 14 such that electrical current between the electrodes is measured to determine the presence of the irrigation fluid in the first lumen 14. Alternatively, the fluid sensor could include a light emitting diode and a light sensing element that is capable of detecting the presence of the irrigation fluid 33 based the color of the fluid being detected in the first lumen 14. In other embodiments, the fluid sensor could include a small reservoir containing a physical sensor monitoring the position of a buoy.

According to some embodiments, the valve system 52 communicates to the vacuum pump 11 that it is flooding the wound enclosure 16 with irrigation fluid in the second mode of operation, which triggers the vacuum pump 11 to enter a specific state in which it is monitoring various operating characteristics, such as the pressure in the first lumen 14, pressure in the second lumen 24, the pump activation settings, the pressure at the vacuum pump 11, and/or the presence of instillation fluid in the first lumen 24.

According to some embodiments, the communication between the vacuum pump 11, valve system 52, and/or controller 70 is done via a wired connection such as USB or a digital ON/OFF switch, or wireless via Internet, wifi, BlueTooth, or other wireless communication protocols.

Figure 4A:
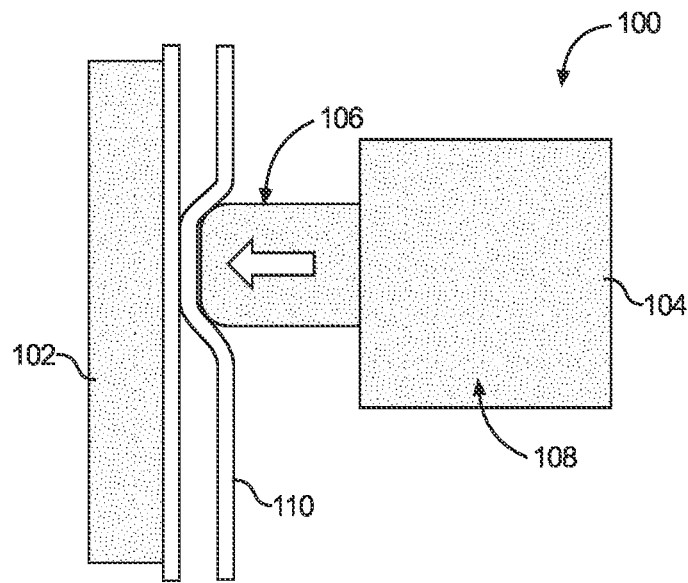
FIG. 4A depicts a valve in a closed position according to one embodiment of the disclosure.
Figure 4B:
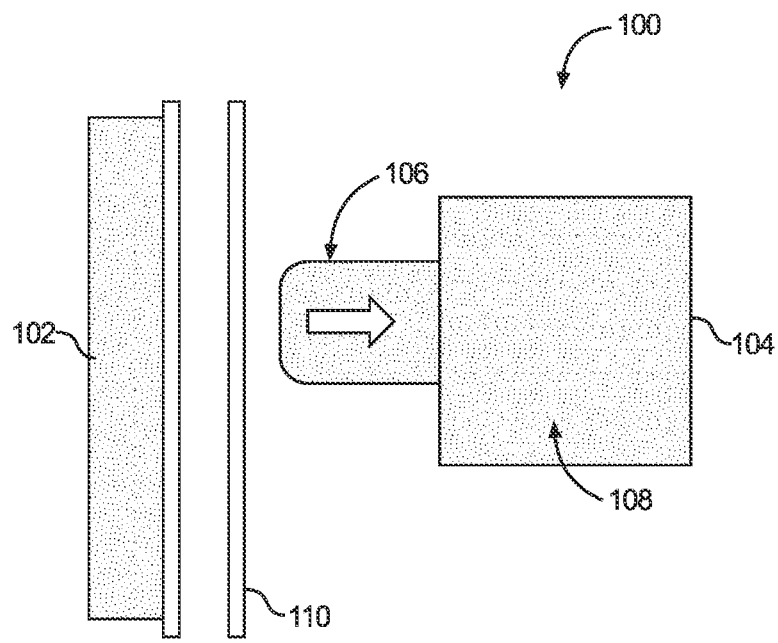
FIG. 4B depicts the valve of FIG. 4A in the open position according to one embodiment of the disclosure.

According to another aspect of the disclosure, valve system 52 includes one or more of valves 54a, 54b, and 54c designed to pinch a flexible lumen to close the valve as appropriate. In certain embodiments, the valves 54a, 54b, and 54c are integrated into a single component instillation device designed to be reusable, while the lumens being pinched are disposable. For example, and with reference to FIG. 4A and FIG. 4B, an exemplary valve 100 is depicted. The valve includes a back wall 102 and a pinching mechanism 104. The pinching mechanism 104 includes a shaft 106 operable to move back and forth as compared to the back wall 102. An actuator 108 (e.g., a solenoid actuator) is operatively connected to the shaft 106 for moving the shaft 106 in an appropriate direction. In operation, a flexible lumen 110 is disposed between the back wall 102 and the pinching mechanism 104. When the valve 100 is intended to be in the closed position as shown in FIG. 4A, the actuator 108 is configured to position the shaft 106 towards the back wall 102 to pinch/close the lumen 110. When the valve 100 is intended to be in the open position as shown in FIG. 4B, the actuator 108 is configured to position the shaft away from the back wall 102 to un-pinch/open the lumen 110.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A wound therapy system for delivering reduced pressure and irrigation fluid to a wound site, the system comprising:
 a wound enclosure configured to form a substantially sealed volume around the wound site;
 a wound exudate collection canister;
 a primary pressure source configured to deliver the reduced pressure to the substantially sealed volume and deliver exudate collected from the wound site to the wound exudate collection canister through a first lumen;
 a secondary pressure source configured to deliver a secondary pressure to the substantially sealed volume through a second lumen;
 a fluid source configured to deliver irrigation fluid to the substantially sealed volume through the second lumen; and
 a valve system fluidly coupled to the secondary pressure source and the fluid source, the valve system operable to selectively couple the secondary pressure source to the second lumen for delivering the secondary pressure to the substantially sealed volume independently of the irrigation fluid and selectively couple the fluid source to the second lumen for delivering the irrigation fluid to the substantially sealed volume independently of the secondary pressure,
 wherein the wound therapy system includes:
 a first mode of operation in which the primary pressure source delivers reduced pressure to the substantially sealed volume through the first lumen while the secondary pressure source delivers the secondary pressure to the substantially sealed volume through the second lumen and the valve system prevents delivery of the irrigation fluid to the substantially sealed volume through the second lumen; and
 a second mode of operation in which the primary pressure source delivers reduced pressure to the substantially sealed volume through the first lumen while the fluid source delivers irrigation fluid to the substantially sealed volume through the second lumen and the valve system prevents delivery of the secondary pressure to the substantially sealed volume through the second lumen.

2. The wound therapy system of claim 1 wherein the valve system is further operable to selectively couple the secondary pressure source and the fluid source to the second lumen simultaneously, the wound therapy system further comprising a flushing mode of operation in which the primary pressure source delivers reduced pressure to the substantially sealed volume through the first lumen while simultaneously delivering secondary pressure from the secondary pressure source and irrigation fluid from the fluid source to the substantially sealed volume through the second lumen.

3. The wound therapy system of claim 1 wherein the valve system is further operable to fluidly couple the secondary pressure source to the first lumen such that the secondary pressure delivered from the secondary pressure source bypasses the wound enclosure during the second mode of operation.

4. The wound therapy system of claim 1 further comprising a dwelling mode of operation in which the primary pressure source delivers reduced pressure to the substantially sealed volume through the first lumen while the valve system prevents the secondary pressure source from delivering the secondary pressure to the substantially sealed volume and prevents the fluid source from delivering irrigation fluid to the substantially sealed volume.

5. The wound therapy system of claim 4 wherein the valve system is configured to fluidly couple the secondary pressure source to the first lumen such that the secondary pressure delivered from the secondary pressure source bypasses the wound enclosure during the dwelling mode of operation.

6. The wound therapy system of claim 4 further comprising:
 a pressure sensor for measuring pressure within at least one of the first lumen and the second lumen; and
 a controller configured to receive pressure measurements from the pressure sensor and to communicate with the valve system for switching between the first, second, and dwelling modes of operation based at least in part on the pressure measurements received from the pressure sensor.

7. The system of claim 4 wherein the primary pressure source is configured to deliver variable reduced pressure to the substantially sealed volume according to a variable pressure cycle during at least the dwelling mode of operation.

8. The wound therapy system of claim 1 wherein the valve system is operable to switch from the first mode of operation to the second mode of operation based at least in part on predetermined time intervals.

9. The wound therapy system of claim 1 wherein a length of time in which the valve system is in the second mode of operation is based at least in part on a size measurement of the wound site.

10. The wound therapy system of claim 1 further comprising an irrigation fluid collection canister fluidly connected to the first lumen between the wound exudate collection canister and the wound enclosure for collecting irrigation fluid from the wound site.

11. The wound therapy system of claim 1 further comprising a fluid sensor configured and positioned for detecting irrigation fluid in the first lumen.

12. A method for delivering reduced pressure and irrigation fluid to a wound site, the method comprising:
 providing a wound therapy system, the wound therapy system including:
 a wound enclosure configured to form a substantially sealed volume around the wound site,
 a wound exudate collection canister,
 a primary pressure source configured to deliver the reduced pressure to the substantially sealed volume and deliver exudate collected from the wound site to the wound exudate collection canister through a first lumen,
 a secondary pressure source configured to deliver a secondary pressure to the substantially sealed volume through a second lumen,
 a fluid source configured to deliver irrigation fluid to the substantially sealed volume through the second lumen, and
 a valve system fluidly coupled to the secondary pressure source and the fluid source, the valve system operable to selectively couple the secondary pressure source to the second lumen for delivering the secondary pressure to the substantially sealed volume independently of the irrigation fluid and selectively couple the fluid source to the second lumen for delivering the irrigation fluid to the substantially sealed volume independently of the secondary pressure;

delivering secondary pressure from the secondary pressure source to the wound enclosure through a second lumen while the valve system prevents delivery of the irrigation fluid to the substantially sealed volume through the second lumen during a first mode of operation;

delivering irrigation fluid from the fluid source to the wound enclosure through the second lumen while the valve system prevents delivery of the secondary pressure to the substantially sealed volume through the second lumen during a second mode of operation;

preventing the delivery of both the secondary pressure and the irrigation fluid to the wound enclosure during a third mode of operation; and continuously delivering reduced pressure from the primary pressure source to the wound enclosure through a first lumen during each of the first mode of operation, the second mode of operation, and the third mode of operation.

13. The method of claim 12 wherein the secondary pressure from the secondary pressure source is delivered to the first lumen while bypassing the wound enclosure during the second mode of operation and the third mode of operation.

14. The method of claim 13 further comprising selectively delivering secondary pressure to the first lumen for managing a pressure in the first lumen during the third mode of operation.

15. The method of claim 12 further comprising:
switching from the first mode of operation to the second mode of operation to initiate an irrigation therapy session;
switching from the second mode of operation to the third mode of operation to perform the irrigation therapy session; and
switching from the third mode of operation back to the first mode of operation to end the irrigation therapy session.

16. The method of claim 13 further wherein the switching from the second mode of operation to the third mode of operation is based at least in part on detecting irrigation fluid in the second lumen.

17. The method of claim 11 further comprising delivering secondary pressure and irrigation fluid to the wound enclosure through the second lumen during a fourth mode of operation.

18. A wound therapy system for delivering reduced pressure and irrigation fluid to a wound site, the system comprising:

a wound enclosure configured to form a substantially sealed volume around the wound site;
a wound exudate collection canister;
a primary pressure source configured to deliver the reduced pressure to the substantially sealed volume and deliver exudate collected from the wound site to the wound exudate collection canister through a first lumen;
a secondary pressure source configured to deliver a secondary pressure to the substantially sealed volume through a second lumen;
a fluid source configured to deliver irrigation fluid to the substantially sealed volume through the second lumen; and
a valve system fluidly coupled to the secondary pressure source and the fluid source, the valve system operable to:
selectively couple the secondary pressure source to the second lumen for delivering the secondary pressure to the substantially sealed volume,
selectively couple the fluid source to the second lumen for delivering the irrigation fluid to the substantially sealed volume, and
selectively couple the secondary pressure source to the first lumen for bypassing the wound enclosure,
wherein the wound therapy system includes a first mode of operation wherein the secondary pressure source is coupled to the second lumen for delivering the secondary pressure to the substantially sealed volume and a second mode of operation wherein the fluid source is coupled to the second lumen and the secondary pressure source is coupled to the first lumen for delivering the irrigation fluid to the substantially sealed volume while secondary pressure delivered from the secondary pressure source bypasses the wound enclosure.

19. The wound therapy system of claim 18 wherein the primary pressure source delivers reduced pressure to the substantially sealed volume through the first lumen during the first mode of operation and during the second mode of operation.

20. The wound therapy system of claim 19 further comprising a flushing mode of operation in which the primary pressure source delivers reduced pressure to the substantially sealed volume through the first lumen while simultaneously delivering secondary pressure from the secondary pressure source and irrigation fluid from the fluid source to the substantially sealed volume through the second lumen.

21. The wound therapy system of claim 19 further comprising a dwelling mode of operation in which the primary pressure source delivers reduced pressure to the substantially sealed volume through the first lumen while the valve system prevents the secondary pressure source from delivering the secondary pressure to the substantially sealed volume and prevents the fluid source from delivering irrigation fluid to the substantially sealed volume.

* * * * *